(12) United States Patent
Hultgren

(10) Patent No.: US 12,295,725 B2
(45) Date of Patent: May 13, 2025

(54) MOTION ADJUSTMENT PREDICTION SYSTEM

(71) Applicant: Bruce Willard Hultgren, Victoria, MN (US)

(72) Inventor: Bruce Willard Hultgren, Victoria, MN (US)

(73) Assignee: HULTGREN DENTAL TECHNOLOGIES, LLC, Victoria, MN (US)

( * ) Notice: Subject to any disclaimer, the term of this patent is extended or adjusted under 35 U.S.C. 154(b) by 785 days.

(21) Appl. No.: 16/823,056

(22) Filed: Mar. 18, 2020

(65) Prior Publication Data
US 2020/0297245 A1 Sep. 24, 2020

Related U.S. Application Data

(60) Provisional application No. 62/941,355, filed on Nov. 27, 2019, provisional application No. 62/822,044, filed on Mar. 21, 2019.

(51) Int. Cl.
A61B 5/11 (2006.01)
A61C 5/77 (2017.01)
(Continued)

(52) U.S. Cl.
CPC .......... *A61B 5/1111* (2013.01); *A61B 5/1128* (2013.01); *A61C 5/77* (2017.02);
(Continued)

(58) Field of Classification Search
CPC ....... A61B 5/1111; A61B 5/1128; A61C 5/77; A61C 7/002; A61C 9/0053; A61C 11/00; A61C 13/0004
See application file for complete search history.

(56) References Cited

U.S. PATENT DOCUMENTS 4,169,314 A * 10/1979 Mercer .................. A61C 11/08
433/60
4,859,181 A * 8/1989 Neumeyer ............ A61B 5/1114
433/69
(Continued)

FOREIGN PATENT DOCUMENTS

WO 9915100 A1 4/1999
WO 2002032340 A2 4/2002
(Continued)

OTHER PUBLICATIONS

PCT International Search Report and Written Opinion in PCT/US2016/039354, mailed Sep. 12, 2016, 19 pages.
(Continued)

*Primary Examiner* — Nicholas D Lucchesi
(74) *Attorney, Agent, or Firm* — Husch Blackwell LLP; Andrew C. Landsman

(57) ABSTRACT

A motion adjustment prediction system is described. A scan of a dentition is performed to generate a digital dental model from which a position and orientation of each tooth in the upper and lower dental arches of the dentition is determined with respect to each other tooth. A dentition motion assessment is performed to capture motion data representing a movement of the dental arches relative to each other. A dental treatment plan with dentition adjustment is determined based on the scan and the dentition motion assessment. The dentition adjustment can include a restoration preparation, such as a crown or a bridge, or can include an orthodontic alignment. A motion adjustment is predicted based on the dentition adjustment, and the dental treatment plan is modified based on the predicted motion adjustment.

13 Claims, 7 Drawing Sheets

(51) Int. Cl.
  *A61C 7/00* (2006.01)
  *A61C 9/00* (2006.01)
  *A61C 11/00* (2006.01)
  *A61C 13/00* (2006.01)
(52) U.S. Cl.
  CPC ............ *A61C 7/002* (2013.01); *A61C 9/0053* (2013.01); *A61C 11/00* (2013.01); *A61C 13/0004* (2013.01)

(56) References Cited

U.S. PATENT DOCUMENTS

| | | | | |
|---|---|---|---|---|
| 6,152,731 | A * | 11/2000 | Jordan | A61C 13/0003 433/69 |
| 6,808,659 | B2 * | 10/2004 | Schulman | A61K 6/84 29/896.1 |
| 6,915,178 | B2 * | 7/2005 | O'Brien | A61C 13/0004 700/118 |
| 7,118,375 | B2 * | 10/2006 | Durbin | B33Y 80/00 433/68 |
| 7,160,110 | B2 | 1/2007 | Imgrund | |
| 7,824,346 | B2 * | 11/2010 | Marshall | G16H 50/50 600/595 |
| 8,200,462 | B2 * | 6/2012 | Marshall | A61C 13/0004 703/11 |
| 8,366,445 | B2 | 2/2013 | Vuillemot | |
| 8,753,114 | B2 | 6/2014 | Vuillemot | |
| 9,125,712 | B2 | 9/2015 | Kraemer | |
| 9,848,964 | B2 | 12/2017 | Hultgren | |
| 9,861,458 | B2 | 1/2018 | Hultgren | |
| 10,201,401 | B2 | 2/2019 | Hultgren | |
| 10,265,150 | B2 | 4/2019 | Hultgren | |
| 2005/0042577 | A1 * | 2/2005 | Kvitrud | A61C 5/77 433/218 |
| 2005/0095562 | A1 * | 5/2005 | Sporbert | G16H 20/40 433/215 |
| 2009/0068617 | A1 * | 3/2009 | Lauren | A61C 5/77 433/213 |
| 2009/0148816 | A1 * | 6/2009 | Marshall | A61C 5/77 433/223 |
| 2009/0316966 | A1 * | 12/2009 | Marshall | G06T 19/00 382/128 |
| 2011/0008751 | A1 * | 1/2011 | Pettersson | A61C 5/77 433/167 |
| 2011/0212420 | A1 * | 9/2011 | Vuillemot | A61C 13/206 433/215 |
| 2012/0291284 | A1 * | 11/2012 | Warden | A61C 13/34 29/896.1 |
| 2013/0066598 | A1 | 3/2013 | Fisker et al. | |
| 2013/0073265 | A1 * | 3/2013 | Kraemer | A61C 19/045 703/1 |
| 2013/0130202 | A1 * | 5/2013 | Vuillemot | A61C 13/0003 433/213 |
| 2014/0255877 | A1 | 9/2014 | Schweiger | |
| 2015/0000677 | A1 * | 1/2015 | Magness | A61F 5/566 128/861 |
| 2015/0019176 | A1 * | 1/2015 | Presswood | G06F 30/00 703/1 |
| 2015/0075542 | A1 * | 3/2015 | Robichaud | A61F 5/566 128/861 |
| 2015/0238280 | A1 * | 8/2015 | Wu | A61C 7/002 433/24 |
| 2015/0238283 | A1 * | 8/2015 | Tanugula | G06F 30/00 700/98 |
| 2015/0305839 | A1 * | 10/2015 | Hultgren | A61B 5/1111 433/213 |
| 2016/0135925 | A1 * | 5/2016 | Mason | A61C 7/002 703/2 |
| 2016/0175076 | A1 * | 6/2016 | Hultgren | A61C 9/0053 433/27 |
| 2016/0199216 | A1 * | 7/2016 | Cam | A61F 5/566 128/848 |
| 2017/0312065 | A1 | 11/2017 | Marshall | |
| 2018/0078342 | A1 * | 3/2018 | Gardner | A61C 7/36 |
| 2018/0078344 | A1 * | 3/2018 | Falkel | A61C 7/36 |
| 2019/0000592 | A1 | 1/2019 | Cam et al. | |

FOREIGN PATENT DOCUMENTS

| | | |
|---|---|---|
| WO | 2016198934 A1 | 12/2016 |
| WO | 2018154485 A1 | 8/2018 |

OTHER PUBLICATIONS

Kumar Y, Janardan R, Larson B, Moon J., Improved segmentation of teeth in dental models. Computer-Aided Design and Applications, 8(2), 2011, pp. 211-224, published by CAD Solutions, LLC, of Lane Aurora, IL.

PCT International Searching Authority; PCT International Search Report and Written Opinion for PCT/US2020/023295; mailed May 13, 2020, 17 pages.

* cited by examiner

MOTION ADJUSTMENT PREDICTION SYSTEM

CROSS-REFERENCE TO RELATED APPLICATIONS

This application claims priority to U.S. Application No. 62/822,044, filed on Mar. 21, 2019, and to U.S. Application No. 62/941,355, filed on Nov. 27, 2019, the disclosures of which are hereby incorporated by reference in their entireties.

BACKGROUND

Dental procedures are often performed to make adjustments to a patient's dentition. Examples of common adjustments that are made include occlusal equilibration, orthodontic alignment of the teeth (such as using braces), installation of dental restorations (including dental implants and crowns) and surgical adjustments (such as implant-supported dentures or orthognathic surgery).

Whenever an adjustment is made to the teeth, it is important for the dentist to avoid making changes that will cause interference with teeth of the opposing dentition. For example, if the adjustment results in a tooth or restoration that is extruded (e.g., too tall and not matching the opposing teeth vertically), an interference will occur between the tooth and the opposing teeth when the patient bites down. As a result, efforts are made to avoid introducing such interference.

However, even with efforts to avoid introducing adjustment-based interference, further changes can occur in the patient's jaw motion as a result of adjustments made in the patient's dentition. Such changes can result in undesirable interference.

SUMMARY

In general terms, this disclosure is directed to a motion adjustment prediction system. In one possible configuration and by non-limiting example, the motion adjustment prediction system is used to predict a motion adjustment of a jaw resulting from a dentition adjustment defined by a dental treatment plan. In further configurations, the predicted motion adjustment can be used to modify the dental treatment plan to accommodate the predicted motion adjustment.

One aspect is a method of analyzing a dental treatment plan, the method comprising performing a scan of a dentition; performing a dentition motion assessment; determining a dental treatment plan with a dentition adjustment based on the scan and the dentition motion assessment; predicting a motion adjustment based on the dentition adjustment; and modifying the dental treatment plan based on the predicted motion adjustment.

Another aspect is a system for analyzing a dental treatment plan, the system comprising a scanner configured to perform a scan of dentition; a motion capture station configured to perform a dentition motion assessment; and a treatment plan generation system configured to determine a dental treatment plan with a dentition adjustment based on the scan and the dentition motion assessment, predict a motion adjustment based on the dentition adjustment, and modify the dental treatment plan based on the predicted motion adjustment.

A further aspect is a method of predicting a motion adjustment responsive to a restoration preparation, the method comprising: performing a scan of dentition; performing a dentition motion assessment; determining a restoration preparation and a restorative material based on the scan and the dentition motion assessment; predicting a motion adjustment based on the restoration preparation; determining whether the restorative material and the restoration preparation cause an interference based on the predicted motion adjustment; in response to a determination that the restorative material and the restoration preparation cause the interference, modifying one or more of the restorative material and the restoration preparation; and in response to a determination that the restorative material and the restoration preparation do not cause the interference, proceeding to perform the restoration preparation.

A yet further aspect is a method of predicting a motion adjustment responsive to a dental alignment, the method comprising performing a scan of dentition; performing a dentition motion assessment; determining a dental alignment plan based on the scan and the dentition motion assessment; predicting a motion adjustment based on the dental alignment plan; identifying and analyzing interference based on the predicted motion adjustment; and modifying the dental alignment to reduce the interference.

These and other aspects and embodiments are described in greater detail below, in reference to the attached drawing figures.

DETAILED DESCRIPTION

Figure 1:
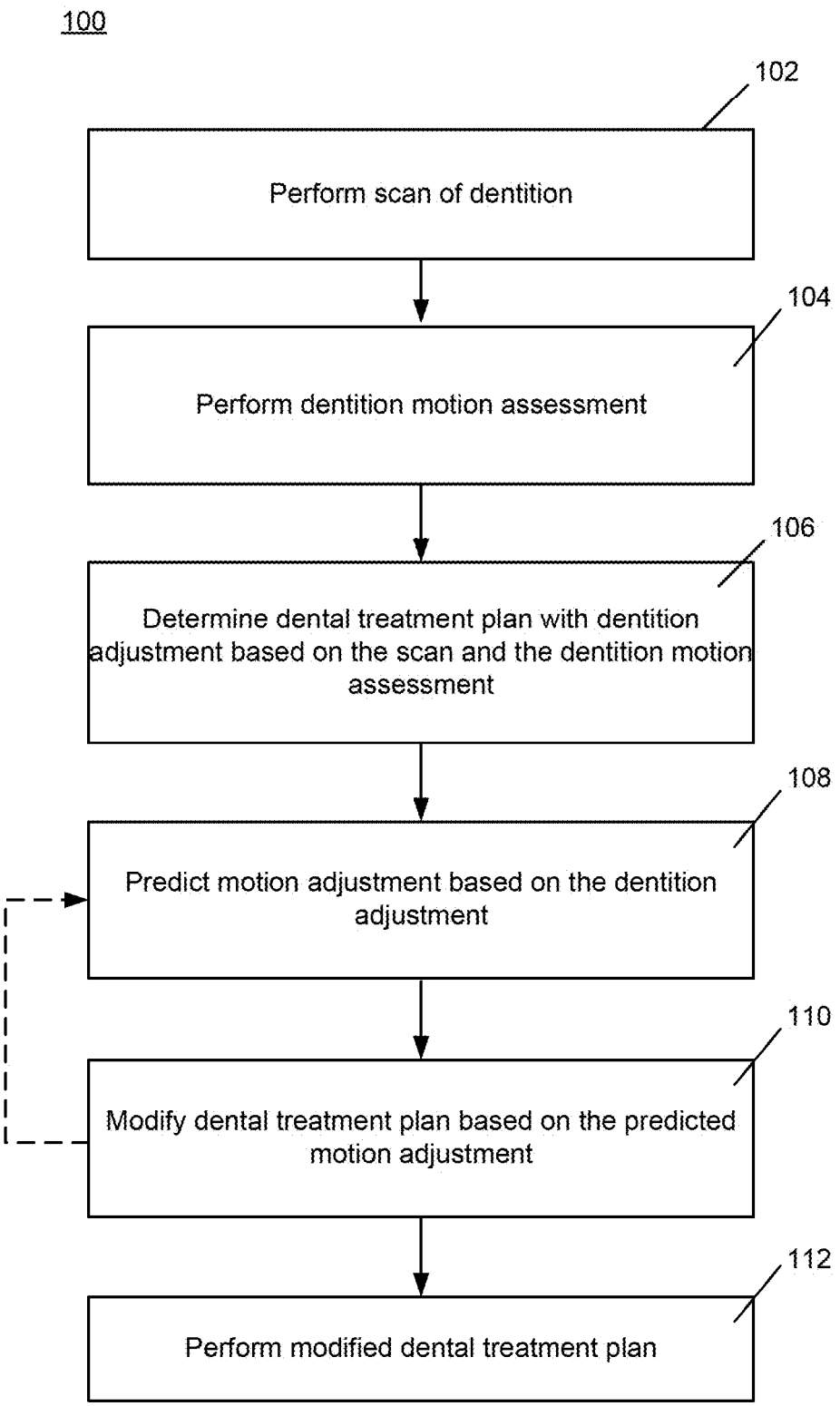
FIG. 1 is a flow chart illustrating an example method of analyzing a dental treatment plan.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

A patient's dentition consists of teeth of both upper and lower dental arches on the upper and lower jaw, respectively. Certain dental procedures performed by a dentist on the patient involve adjusting a tooth or teeth of one or both dental arches. In some examples, the dental procedure can involve occlusal equilibration. In other examples, the dental procedure can involve dental restorations, including dental implants, bridges, and/or crowns. In further examples, the dental procedure can involve orthodontic alignment of the teeth, including use of braces. In yet further examples, the dental procedure can involve surgical adjustments, including implant-supported denture surgeries and orthognathic surgeries. Moreover, the dental procedure can involve a combination of occlusal equilibration, dental restorations, orthodontic alignment of teeth, and surgeries.

Whenever an adjustment is made to a tooth, there is a potential that the adjustment will cause interference with teeth of the opposing dental arch. For example, if the adjustment results in the tooth being extruded (e.g., too tall and not matching the opposing teeth vertically), an interference will occur between the tooth and the opposing teeth when the patient bites down. Additionally, changes can occur in the patient's jaw motion as a result of the adjustment made to the tooth. For example, prior to the dental procedure, the patient's dentition may already have some interference that has caused the patient's jaw motion to be restricted, such as a shape of the tooth or the way in which the tooth fits together with an opposing tooth that restricts the jaw to only move so far vertically, anteroposteriorly, and transversely (e.g., up and down, front and back, and side to side). In some situations, the interference is removed as a result of the adjustment to the tooth, causing the jaw motion to adjust and have a less restricted, more extensible movement in one or more directions, which in turn causes the teeth to move relative to one another in different ways. For example, a particular tooth can now move further vertically, anteroposteriorly, or transversely (e.g., further up or down, front or back, or side to side), which changes the way the tooth fits or interacts with teeth of the opposing dental arch, and can cause an interference that affects the patient's bite or chewing.

Often times, when generating and performing a dental treatment plan that involves a dentition adjustment, a dentist only takes into account and proactively avoids interferences with opposing teeth directly created by the dentition adjustment, and does not consider subsequent jaw motion changes and corresponding effects. As a result, when the dentition is adjusted, a corresponding jaw motion adjustment can occur that was not accounted for in the dental treatment plan. Even if the dentist performs a scan post-procedure, this scan is static (e.g., comprised of multiple static bites) and may not capture interferences created from the jaw motion adjustment. Accordingly, the patient may leave the dentist office unaware, but as the patient more dynamically moves their jaw (e.g., when chewing food), the patient may then notice and experience discomfort or pain due to the interference requiring the patient to return to the dentist for a correction. Once the interference is identified, the patient will need to spend additional time at the dentist office for the dentist to modify the preparation and/or materials used for the dental procedure, and may still need to come back for a later visit if the dentist needs to order new materials (e.g., a new crown) based on the changes caused by the interference. In other scenarios, the motion of the jaw may change slowly over time as a result of the dentition adjustment causing a new interference. Similarly, additional visits to the dentist office will be required once effects of the new interference are noticed by the patient in order to identify and correct the new interference.

To proactively avoid interferences caused by both dentition adjustment and jaw motion adjustment and prevent a patient from enduring multiple unnecessary office visits, embodiments described herein can be implemented to predict a motion adjustment responsive to a dental treatment plan including a dentition adjustment. The dental treatment plan can then be modified to accommodate the predicted motion adjustment prior to performance of the dentition adjustment. Additionally, data collected to predict the motion adjustment, such as scans of the patient's dentition, motion data from dentition motion assessments, and various digital models generated therefrom, and data associated with the predicted motion adjustment, such as interference boundaries, can be stored for use and/or reference in future dental procedures.

FIG. 1 is a flow chart illustrating an example method 100 of analyzing a dental treatment plan. The method 100 can be implemented, for example, by the example patient evaluation system 120 described herein with reference to FIG. 2 through FIG. 4 below. In this example, the method 100 includes operations 102, 104, 106, 108, 110, and 112.

Prior to performing a dental procedure, a scan of a patient's dentition is performed at operation 102. The scan identifies a position and an orientation of each tooth in the upper and lower dental arches of the patient's dentition with respect to each other tooth.

At operation 104, a dentition motion assessment is performed. The dentition motion assessment captures motion data representing the movement of the patient's dental arches relative to each other. For example, the dentition motion assessment captures how each tooth in the upper and lower dental arches move with respect to one another.

In some embodiments, a pre-treatment interference boundary can be determined utilizing the position and orientation of each tooth in the dental arches provided by the scan and the movement of each tooth in the dental arches provided by the motion data. The pre-treatment interference boundary is a boundary of function between teeth of opposing dental arches before a treatment plan has been implemented. The pre-treatment interference boundary is defined by the interface or interaction between the teeth on the opposing dental arches. For example, the pre-treatment interference boundary indicates how far any of the teeth can move vertically, anteroposteriorly, and transversely. If a tooth extends or crosses over the pre-treatment interference boundary in one or more planes, an interference with teeth of the opposing dental arch of the dentition is created.

To provide additional context, the pre-treatment interference boundary may be analogous to a functionally generated pathway (FGP) of occlusion. An FGP is generated based on registered paths of movement of occlusal surfaces of the teeth of one dental arch, to the teeth or occlusion rims of the opposing dental arch that are recorded using a medium. An example technique for generating an FGP includes adapting a material over the occlusal surface of a tooth or teeth and having the patient occlude the teeth in the intercuspal position and move the lower jaw throughout all excursions. This allows the opposing teeth to three-dimensionally record border movements in each jaw position in the material to define a boundary of function between teeth of opposing dental arches. However, the pre-treatment interference boundary may be determined more quickly and accurately (and with less inconvenience to the patient) based on the position and orientation of each tooth in the dental arches provided by the scan and the movement of each tooth in the dental arches provided by the motion data.

An interference boundary can be thought of as a surface that would be generated if a tray, containing a pliable material such as paste or gel, was mounted to one of the dental arches, and then the patient were to bite down into the material and move the opposing dentition around in all directions. The result would be a surface that records the furthest extent that the teeth can reach. For example, a surface that records perimeters of a boundary defining a vertical, anteroposterior, and traversal reach of the teeth. This same or similar type of an interference boundary can be generated and stored digitally.

At operation 106, a dental treatment plan with a dentition adjustment is determined based on the scan and the dentition motion assessment. The dentition adjustment can involve any kind of change in the structure or positions of the teeth. To provide some examples, the dentition adjustment can include a removal, re-shaping, and/or re-alignment of a portion or entirety of a tooth or teeth on one or both dental arches of the patient's dentition. When determining the dental treatment plan, the adjustment to a tooth or teeth of one dental arch of the dentition is defined to avoid an interference with teeth of the opposing dental arch of the dentition. For example, the scan performed at operation 102 and the motion data obtained from the dentition motion assessment performed at operation 104 are utilized to visualize a position and orientation of a tooth associated with the dentition adjustment and how the tooth can move vertically, anteroposteriorly, and transversely to ensure that the dentition adjustment does not move or adjust the tooth beyond the confines of the pre-treatment interference boundary (e.g., does not violate the pre-treatment interference boundary to avoid creating an interference).

However, even with efforts to avoid introducing interference by accounting for the dentition adjustment, changes can occur in the patient's jaw motion as a result of adjustments made to the patient's dentition. Additionally or alternatively, changes in the patient's jaw motion can be caused by changes to joints of the jaw (e.g., as a result of surgery). Such changes in jaw motion can also result in undesirable interference. Therefore, to further bolster efforts to avoid introducing interference, the changes occurring to the patient's jaw motion as a result of the dentition adjustment can also be accounted for by predicting a motion adjustment based on the dentition adjustment at operation 108. For example, a determination is made as to whether an interference will be removed after the dentition adjustment (e.g., whether an already existing interference within patient's dentition due to a shape of a tooth or current interactions between teeth will be removed) and, if so, a determination of associated effects of the interference removal (e.g., a determination of changes to the jaw motion) is made to predict the motion adjustment. In some examples, because the jaw's range of motion influences how far a tooth or teeth may be able to move in direction and magnitude, the associated effects of the removal can cause a change to the pre-treatment interference boundary. Thus, a post-dentition adjustment interference boundary is predicted to represent the interference boundary following the dentition adjustment and removal of the interference.

At operation 110, the dental treatment plan is modified based on the predicted motion adjustment. For example, if it is determined that the dentition adjustment proposed by the dental treatment plan will cause changes to the jaw motion, the dental treatment plan is modified to accommodate the predicted motion adjustment so that the dental treatment plan continues to avoid introducing any interference. As one example, a jaw motion change may result in a change to the pre-treatment interference boundary. For example, the jaw may now be more or less extensible, and the boundary may change accordingly. Therefore, the dental treatment plan is modified to ensure that the dentition adjustment made does not go beyond the confines of or violate the predicted post-dentition adjustment interference boundary. Accordingly, the modified dental treatment plan proactively accounts for (e.g., in order to avoid) interferences caused by both the dentition adjustment and subsequent motion adjustment of the jaw.

In some embodiments the operations 108 and 110 can be repeated one or more times until interference is eliminated, or until the interference is less than a predetermined amount. For example, the predetermined amount is less than a predetermined overlap distance. Once the interference is eliminated, or the interference is less than the predetermined amount, the modified dental treatment plan can be performed at operation 112.

Figure 2:
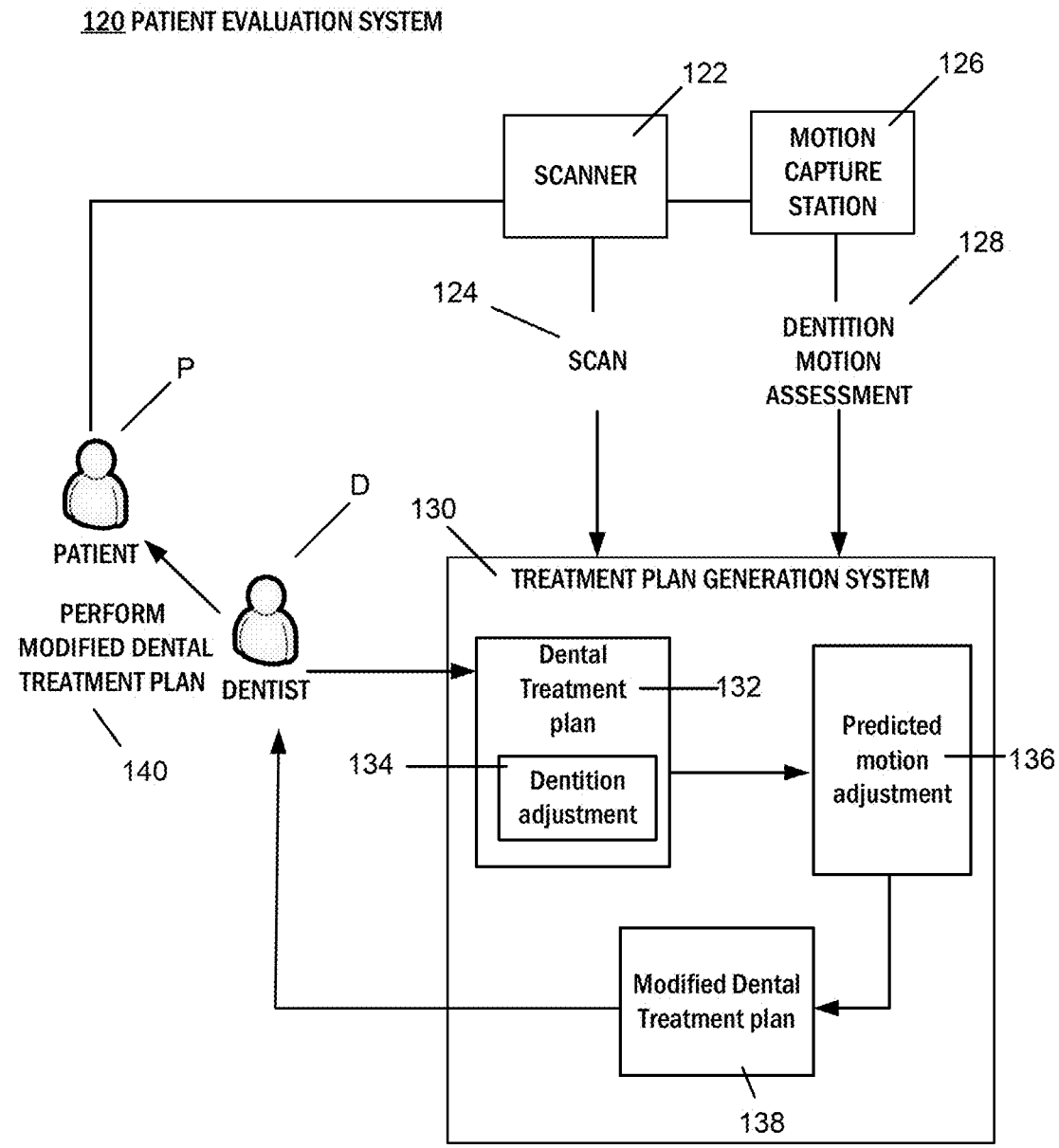
FIG. 2 is a schematic block diagram illustrating an example patient evaluation system for analyzing a dental treatment plan.

FIG. 2 is a schematic block diagram illustrating an example patient evaluation system 120 for implementing the method 100 of analyzing a dental treatment plan described in FIG. 1. The patient evaluation system 120 includes a scanner 122, a motion capture station 126, and a treatment plan generation system 130.

Prior to a dentist D performing a dental procedure on a patient P, a scan 124 of dentition of the patient P is captured by the scanner 122 to perform operation 102 and a dentition motion assessment 128 is performed on patient P by the motion capture station 126 to perform operation 104. The scan 124 and dentition motion assessment 128 are provided as input to the treatment plan generation system 130.

The scan 124 provides a position and an orientation of each tooth in the upper and lower dental arches of the dentition with respect to each other tooth. The dentition motion assessment 128 comprises motion data providing the movement of the dental arches relative to each other, including how each tooth in the upper and lower dental arches move with respect to one another. In some examples, the dentition motion assessment 128 also provides a pre-treatment interference boundary. In other examples, the treatment plan generation system 130 determines the pre-treatment interference boundary from data associated with the scan 124 and the dentition motion assessment 128. The pre-treatment interference boundary is a boundary of function between teeth of opposing dental arches before a treatment plan has been implemented, and is defined by the interface or interaction between the teeth on the opposing dental arches. For example, the pre-treatment interference boundary indicates how far each particular tooth can move vertically, anteroposteriorly, and transversely. If a tooth extends or crosses over the pre-treatment interference boundary in one or more planes, an interference with teeth of the opposing dental arch of the dentition is created.

Based on the data associated with the scan 124 and dentition motion assessment 128, the treatment plan generation system 130 determines a dental treatment plan 132 that includes a dentition adjustment 134 to perform operation 106. The dentition adjustment 134 can involve any kind of change in the structure or positions of the teeth, such as a removal, re-shaping, and/or re-alignment of a portion or entirety of a tooth or teeth on one or both dental arches of the patient P's dentition, among other examples. When determining the dental treatment plan 132, the dentition adjustment 134 is defined to avoid an interference between a tooth or teeth associated with the dentition adjustment 134 and teeth of the opposing dental arch of the dentition. For example, data from the scan 124 and the dentition motion assessment 128 are utilized to visualize a position and orientation of a tooth or teeth associated with the dentition adjustment 134 and how the tooth or teeth can move vertically, anteroposteriorly, and transversely to ensure that the dentition adjustment does not move or adjust the tooth or teeth beyond the confines of the pre-treatment interference boundary (e.g., does not violate the pre-treatment interference boundary to avoid introducing an interference).

However, because the dental treatment plan 132 includes the dentition adjustment 134 and changes can occur in the patient's jaw motion as a result of the dentition adjustment 134, the treatment plan generation system 130 further determines a predicted motion adjustment 136 based the dentition adjustment 134 to perform operation 108. For example, a determination is made as to whether an interference will be removed after the dentition adjustment 134 and if so, a determination of associated effects of the removal of the interference (e.g., a determination of changes to the jaw motion) is made to determine the predicted motion adjustment 136. In some examples, because the jaw's range of motion influences how far a tooth or teeth may be able to move in direction and magnitude, the associated effects of the removal of the interference can cause a change to the pre-treatment interference boundary. Thus, a post-dentition adjustment interference boundary is predicted to represent the interference boundary following the changes resulting from the removal of the interference.

The treatment plan generation system 130 then uses the predicted motion adjustment 136 to modify the dental treatment plan 132 to create a modified dental treatment plan 138 to perform operation 110. For example, if it is determined that the dentition adjustment 134 of the dental treatment plan 132 will cause changes to the jaw motion, the dental treatment plan 132 is modified to accommodate the predicted motion adjustment so that the dental treatment plan 132 continues to avoid introducing any interference. As one example, a jaw motion change may result in a change to the pre-treatment interference boundary. For example, the jaw may now be more or less extensible, and the boundary may change accordingly. Therefore, the dental treatment plan 132 is modified to the modified dental treatment plan 138 to accommodate the predicted motion adjustment 136. For example, the modified dental treatment plan 138 ensures that the dentition adjustment 134 made does not go beyond the confines of or violate the predicted post-dentition adjustment interference boundary.

To perform operation 112, the treatment plan generation system 130 provides the modified dental treatment plan 138 as output to the dentist D such that the dentist D performs 140 the modified dental treatment plan 138 that proactively avoids introducing interferences potentially caused by both the dentition adjustment 134 and the predicted motion adjustment 136.

Figure 3:
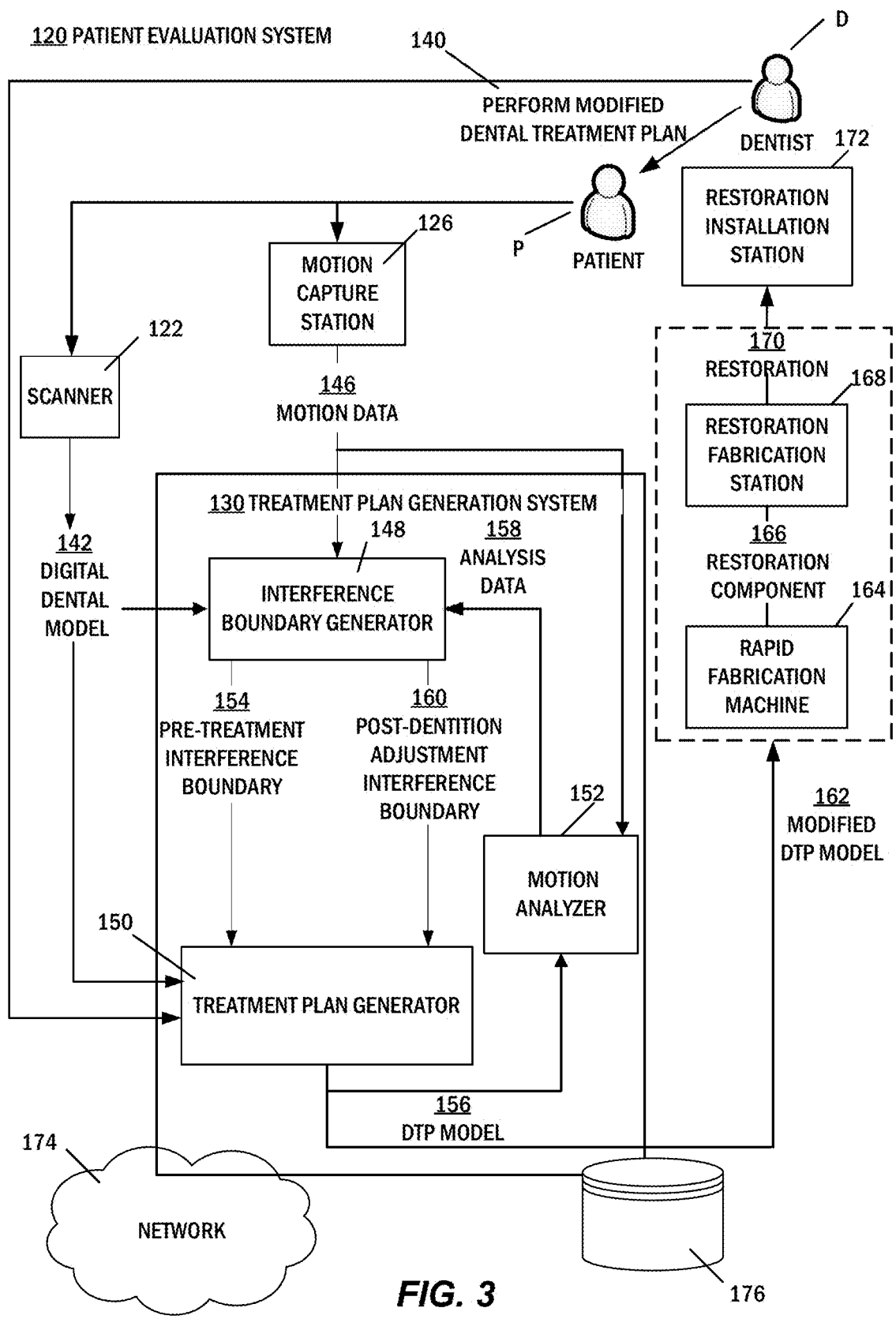
FIG. 3 is another schematic block diagram illustrating an example patient evaluation system for analyzing a dental treatment plan.

FIG. 3 is another schematic block diagram illustrating another example of the patient evaluation system 120, shown in FIG. 2, for implementing the method 100 of analyzing a dental treatment plan described in FIG. 1. The example patient evaluation system 120 includes the scanner 122, the motion capture station 126, and the treatment plan generation system 130 as described in FIG. 2. The treatment plan generation system 130 includes an interference boundary generator 148, a treatment plan generator 150, and a motion analyzer 152. In optional embodiments, the patient evaluation system 120 further comprises a rapid fabrication machine 164 and/or restoration fabrication station 168, and a restoration installation station 172.

In some embodiments, various components of the patient evaluation system 120 may be at least partially located within a physical dental office and/or a dental lab. Additionally, any of the computerized functions could be performed in the dental office, dental lab, or remotely by, or in cooperation with, one or more other computing devices (including client, server, or cloud computing devices), and any number of computing devices can be used to perform all or any part of the system. For example, in some embodiments, the patient evaluation system 120 may comprise a web-based service performing various functions of the system.

The system and methods begin by scanning the dentition of the patient P to perform operation 102. For example, scanner 122 performs the scan 124, from which a position and an orientation of each tooth in the upper and lower dental arches of the dentition is determined with respect to each other tooth. The scanner 122 can be an intraoral scanner, where example intraoral scanners include the Medit Intraoral Scanner, TRIOS Intra Oral Digital Scanner, the Lava Chairside Oral Scanner C.O.S., the Cadent iTero, the Cerec AC, the Cyrtina IntraOral Scanner, and the Lythos Digital Impression System from Ormco. In other embodiments, the dentition of the patient P is captured using other imaging technologies, such as computed tomography (CT) or magnetic resonance imaging (MM). In some examples, the type of CT used is Dental Cone Beam CT (Dental CBCT).

In some examples, the scanner 122 is capable of creating a digital dental model 142, which is a three-dimensional digital representation of the dentition of the patient P from the scan 124. For example, the scanner 122 comprises a laser scanner, a touch probe, or an industrial CT scanner, among other types of scanners capable of creating three-dimensional digital representations. In some embodiments, the scanner 122 generates a point cloud, a polygonal mesh, a parametric model, or voxel data representing the dentition of the patient P.

Some embodiments further include a segmentation tool that analyzes the digital dental model 142 generated from the scanner 122 and segments the model to separate each tooth from adjacent teeth, which is then saved into the digital dental model 142. The segmentation tool can be a part of the scanner 122, or can be a separate component. In some embodiments, the segmentation tool can be one of a variety of tools provided by the treatment plan generator 150 described in detail in FIG. 4. An example of the segmentation tool is an auto-segmentation software application. Auto-segmentation software and related techniques are described in Kumar Y, Janardan R, Larson B, Moon J. Improved segmentation of teeth in dental models. Computer-Aided Design and Applications, 8(2), 2011, 211-224, published by CAD Solutions, LLC, of Lane Aurora, IL Segmentation is useful, for example, to allow individual teeth (or groups of teeth) within the digital dental model 142 to be moved relative to the other teeth when generating the treatment plan using the treatment plan generator 150, discussed in further detail herein.

To perform operation 104, the dentition motion assessment 128 is performed on patient P using the motion capture station 126 to generate motion data 146 representing the movement of the dental arches relative to one another. In some embodiments, the motion capture station 126 generates the motion data 146 from optical measurements of the dental arches that are captured while the dentition of the patient P is moved. In some embodiments, the optical measurements are extracted from image or video data recorded while the dentition of the patient P is moved. Additionally, in some embodiments, the optical measurements are captured indirectly. For example, the optical measurements are extracted from images or video data of one or more devices that are secured to a portion of the dentition of the patient.

In other embodiments, still images are captured of the patient's dentition while the dentition of the patient is positioned in a plurality of bite locations. In some embodiments, image processing techniques are used to determine the positions of the patient's upper and lower arches relative to each other (either directly or based on the positions of attached devices). In some embodiments, the motion data 146 is generated by interpolating between the positions of the upper and lower arches determined from at least some of the captured images.

Examples of the motion capture station 126 are described in U.S. Publication No. 2017/0312065, filed on Apr. 28, 2017, and titled DETERMINING JAW MOVEMENT, the disclosure of which is hereby incorporated by reference in its entirety for all purposes and specifically for description of the motion capture station 126. For example, the motion capture station 126 may comprise a patient assembly that includes a clutch to be worn by the patient P on a dentition of the patient P. The clutch includes a dentition coupling device to couple to the dentition of the patient P and a position indicating system rigidly connected to the dentition coupling device, where the position indicating system emits a plurality of light beams. The motion capture station 126 can also include an imaging system and a motion determining device, where the imaging system captures a plurality of image sets that each include at least one of a plurality of screens upon which the light beams project, and the motion determining device processes the captured image sets to determine the motion of the patient's dentition.

In other embodiments, the motion data 146 is generated using other processes. Further, in some embodiments, the motion data 146 includes transformation matrices that represent the position and orientation of the dental arches. Other embodiments of the motion data 146 are possible as well.

The treatment plan generation system 130 receives the digital dental model 142 and the motion data 146 as input. The treatment plan generation system 130 includes one or more components and/or sub-systems including at least the interference boundary generator 148, the treatment plan generator 150, and the motion analyzer 152.

The interference boundary generator 148 of the treatment plan generation system 130 determines a pre-treatment interference boundary 154 based on the position and orientation of each tooth provided by the digital dental model 142 and the movement of each tooth relative to one another provided by the motion data 146. The pre-treatment interference boundary 154 is a boundary of function between teeth of the dental arch on the upper jaw and teeth of the opposing dental arch on the lower jaw, and is defined by the interface or interaction between the teeth on the opposing dental arches before a treatment plan is implemented. For example, the pre-treatment interference boundary 154 identifies for all possible positions of the dental arches, the boundary at which no teeth from the opposing arch will cross. If any teeth do cross over the pre-treatment interference boundary in one or more planes, an interference with teeth of the opposing dental arch of the dentition is created.

The treatment plan generator 150 of the treatment plan generation system 130 determines the dental treatment plan 132. The dental treatment plan 132 includes at least one dentition adjustment 134 for the patient P. The dentition adjustment 134 involves any kind of change in the structure or positions of the teeth. In one example, the dentition adjustment 134 can be an occlusal equilibration, whereby a surface of a tooth on one or both dental arches is altered (e.g., by raising a surface of the tooth or grinding down the surface of the tooth) to allow the jaw joints to be in the proper anatomical location when the teeth on opposing arches come into contact. In another example, the dentition adjustment 134 can be a restoration preparation or a corresponding temporary or provisional restoration, such as the preparation for a crown or a bridge that involves cutting down and/or re-shaping a portion or entirety of a tooth or teeth, as described in further detail in FIG. 6. In a further example, the dentition adjustment 134 can be a dental alignment, such as an orthodontic alignment, as described in further detail in FIG. 7. In yet further examples, the dentition adjustment 134 involve a dental surgery that reshapes the jaw causing the change in the structure or positions of the teeth.

Typically, the treatment plan generator 150 operates in cooperation with an operator user, such as the dentist D, to receive inputs to generate the dental treatment plan 132. For example, in some embodiments, the treatment plan generator 150 comprises at least one computing device including one or more user input devices through which input from the operator user is received. Using the digital dental model 142, the motion data 146, and the pre-treatment interference boundary 154 determined by the interference boundary generator 148, the treatment plan generator 150, in conjunction with the operator user, can define at least one dentition adjustment 134 of the dental treatment plan 132. Particularly, the dentition adjustment 134 is defined to avoid an adjustment that will cause interference with teeth of the opposing dentition. For example, a tooth or restoration that is recessed from the pre-treatment interference boundary 154 cannot interfere with the opposing dentition, whereas a tooth that projects past the pre-treatment interference boundary 154 will interfere with the movement of the opposing dentition. Therefore, the digital dental model 142, the motion data 146, and the pre-treatment interference boundary 154 are utilized to visualize a position and orientation of a tooth associated with the dentition adjustment 134 and how the tooth can move vertically, anteroposteriorly, and transversely to ensure that the dentition adjustment 134 does not move or adjust the tooth beyond the confines of the pre-treatment interference boundary 154 (e.g., does not violate the pre-treatment interference boundary 154 to avoid introducing an interference).

In some embodiments, the dental treatment plan 132 is generated as three-dimensional digital data that represents a dental treatment plan (DTP) model 156. For example, the DTP model 156 comprises a three-dimensional representation of the dentition of the patient with the dentition adjustment 134.

In some embodiments, the treatment plan generator 150 includes computer-aided-design (CAD) software that generates a graphical display of the digital dental model 142 and, either automatically or in cooperation with the operator user generates the DTP model 156 that identifies the at least one dentition adjustment 134 from the original digital dental model 142. In some embodiments the operator user interacts with and manipulates the DTP model 156 to define the adjustments to be made, as discussed above. In some embodiments, the treatment plan generator 150 comprises digital tools that mimic the tools used by laboratory technicians, as described in greater detail in FIG. 4 below. Additionally, in some embodiments, the treatment plan generator 150 comprises a computing device that partially or fully automates the generation of the DTP model 156.

As described in the example embodiments above, the DTP model 156 is generated to include the dentition adjustment 134 as a simulation of the dentition adjustment (e.g., without the dentition adjustment actually being performed). In other example embodiments, the dentition adjustment 134 can be performed according to the dental treatment plan 132, another scan of the dentition post-dentition adjustment is captured by the scanner 122, and the DTP model 156 is generated based on the post-dentition adjustment scan (e.g., the DTP model 156 is a three-dimensional representation of the patient's dentition after the dentition adjustment has been performed).

The motion analyzer 152 of treatment plan generation system 130 predicts a motion adjustment based on the dentition adjustment 134. For example, the motion analyzer 152 analyzes the DTP model 156, along with the motion data 146, to predict what changes will occur in the patient's jaw motion as a result of the dentition adjustment 134, and then analyzes the DTP model 156 based on the predicted changes in the patient's jaw motion (e.g., to collect analysis data 158).

Various embodiments can be implemented by the motion analyzer 152 to predict the motion adjustment. In one or more of the embodiments, a location of a screw axis of the patient's jaw is determined. The screw axis corresponds to the condyloid process of the temporomandibular joint of the patient P, and is an axis about which the lower jaw rotates and translates along an eminence of a condyle of the condyloid process when in function. Accordingly, the location of the screw axis imposes limitations on a range of motion of the jaw. Mathematical coordinates of the range of motion relative to the patient's dentition can be determined and used as parameters for simulating the motion of the jaw. Other jaw-related characteristics or parameters, such as a flexibility or "sponginess" of the temporomandibular joint, can be determined and used as data input for simulating the motion of the jaw. For example, the DTP model 156 that includes the dentition adjustment 134 can be used in conjunction with the screw axis location and other jaw-related parameters to simulate the motion of the jaw after the dentition adjustment 134, as described in greater detail in FIG. 4, to predict the motion adjustment.

In some embodiments, a post-dentition adjustment interference boundary 160 is predicted based on the analysis data 158 to determine a change from the location of the pre-treatment interference boundary 154. For example, the motion analyzer 152 can provide the analysis data 158 to the interference boundary generator 148, the analysis data 158 including the predicted motion adjustment 136 resulting from the dentition adjustment 134. The interference boundary generator 148 can generate a post-dentition adjustment interference boundary 160 based on the analysis data 158 and the DTP model 156, and provide the post-dentition adjustment interference boundary 160 to the treatment plan generator 150.

The treatment plan generator 150 can then modify the dental treatment plan 132 as needed to create a modified dental treatment plan 138. For example, if it is determined that the dentition adjustment 134 of the dental treatment plan 132 will cause changes to the jaw motion, the dental treatment plan 132 is modified to accommodate the predicted motion adjustment so that the dental treatment plan 132 continues to avoid introducing any interference. As one example, if based on the change between the pre-treatment interference boundary 154 and the post-dentition adjustment interference boundary 160, it is determined that the dentition adjustment 134 proposed by the dental treatment plan 132 will cause an interference to be removed that subsequently will adjust a motion of the jaw, the treatment plan generator 150 modifies the dental treatment plan 132 to accommodate the predicted motion change in the modified dental treatment plan 138. For example, the dentition adjustment 134 can be modified to ensure that a tooth associated with the dentition adjustment 134 does not go beyond the confines of or violate the predicted post-dentition adjustment interference boundary 160. The treatment plan generator 150 can then correspondingly adjust the DTP model 156 to generate a modified DTP model 162 based on the modified dental treatment plan 138.

The treatment plan generation system 130 may store the patient's data including one or more of the scan 124, the digital dental model 142, the dentition motion assessment 128, the motion data 146, the pre-treatment interference boundary 154, the dental treatment plan 132 with dentition adjustment 134, the DTP model 156, the analysis data 158, the post-dentition adjustment interference boundary 160, the modified dental treatment plan 138, and the modified DTP model 162, among other patient data. The patient's data can be used to facilitate and inform future dental procedures. The patient's data may be stored in a database 176 associated with the treatment plan generation system 130 and/or patient evaluation system 120.

In some embodiments, the modified DTP model 162 includes a digital model of a restoration associated with the modified dental treatment plan 138 that can be optionally provided to a rapid fabrication machine 164. In some embodiments, the rapid fabrication machine 164 comprises one or more three-dimensional printers, such as the ProJet line of printers from 3D Systems, Inc. of Rock Hill, South Carolina Another example of the rapid fabrication machine 164 is stereolithography equipment. Yet another example of the rapid fabrication machine 164 is a milling device, such as a computer numerically controlled (CNC) milling device. In some embodiments, the rapid fabrication machine 164 is configured to receive files in the STL format. Other embodiments of the rapid fabrication machine 164 are possible as well.

In some embodiments, the rapid fabrication machine 164 is configured to use the modified DTP model 162 to fabricate the dental restoration component 166. In some embodiments, the dental restoration component 166 is a physical component that is configured to be used as part or all of the dental restoration 170. For example, in some embodiments, the dental restoration component 166 is milled from zirconium or another material that is used directly as a dental restoration 170. In other embodiments, the dental restoration component 166 is a mold formed from wax or another material and is configured to be used indirectly (e.g., through a lost wax casting or ceramic pressing process) to fabricate the dental restoration 170. For example, in some embodiments, the dental restoration 170 is formed using traditional techniques (e.g., stacked porcelain or wax-up). In additional examples, when the rapid fabrication machine 164 is a three-dimensional printer, underlayments and/or frameworks for the dental restoration component 166 can be printed. For example, metal or ceramic underlayments and/or frameworks are printed.

In some embodiments, the restoration fabrication station 168 operates to fabricate the dental restoration 170 for the patient P. In some embodiments, the restoration fabrication station 168 uses the modified DTP model 162 or the dental restoration component 166 produced by the rapid fabrication machine 164. In some embodiments, the dental restoration 170 is a filling, partial crown, full crown, veneer, bridge, complete denture, partial denture, or implant framework. Other embodiments of the dental restoration 170 are possible as well. In some embodiments, the dental restoration 170 is formed from an acrylic, ceramic, or metallic material. In some embodiments, a model of the dentition of the patient P is generated by the rapid fabrication machine 164 using the scan 124 (and/or the digital dental model 142) captured by the scanner 122. In some embodiments, the restoration fabrication station 168 comprises equipment and process to perform some or all of the techniques used in traditional dental laboratories to generate dental restorations. Other embodiments of the restoration fabrication station 168 are possible as well.

In some embodiments, when the dental restoration 170 is a crown, for example, the crown is automatically fabricated based on the modified DTP model 162 to account for both dentition adjustment and jaw motion adjustment. For example, an occlusal surface of the crown is fabricated to correspond with the predicted post-dentition adjustment interference boundary 160. In some embodiments, a default crown structure is used as a starting template that is then adjusted and contoured based on the predicted post-dentition adjustment interference boundary 160. Specifically, the predicted post-dentition adjustment interference boundary 160 is used to define contoured portions of the crown surface that interface with opposing and adjacent teeth to prevent post-dentition adjustment interference. For example, based on the predicted post-dentition adjustment interference boundary 160, one or more rules or parameters are generated to ensure that the post-dentition adjustment interference boundary 160 is not violated in any plane by the crown. In some examples, the rules or parameters are associated with a slope of the sidewalls of the crown, in addition to a height and occlusal surface shape of the crown.

In some embodiments, to perform 140 the modified dental treatment plan 138, the dentist D may seat the dental restoration 170 in the mouth of the patient P or perform another associated dental procedure in accordance with the modified dental treatment plan 138 at the restoration installation station 172. In some embodiments, the dentist D confirms that the dental restoration 170 properly corresponds to the dental preparation (e.g., the dentition adjustment 134) and the dental restoration 170 or other associated dental procedure accounts for any motion changes to the jaw caused by the dental preparation.

Additionally, in some embodiments, various systems, sub-systems, and/or components are connected by network 174. The network 174 is an electronic communication network that facilitates communication between the various systems and components of the patient evaluation system 120 spread across a dental office, a dental lab, and/or web-based platforms. An electronic communication network is a set of computing devices and links between the computing devices. The computing devices in the network 174 use the links to enable communication among the computing devices in the network 174. The network 174 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices.

In various embodiments, the network 174 includes various types of links. For example, the network 174 can include one or both of wired and wireless links, including Bluetooth, ultra-wideband (UWB), 802.11, ZigBee, and other types of wireless links. Furthermore, in various embodiments, the network 174 is implemented at various scales. For example, the network 174 can be implemented as one or more local area networks (LANs), metropolitan area networks, subnets, wide area networks (such as the Internet), or can be implemented at another scale.

Figure 4:
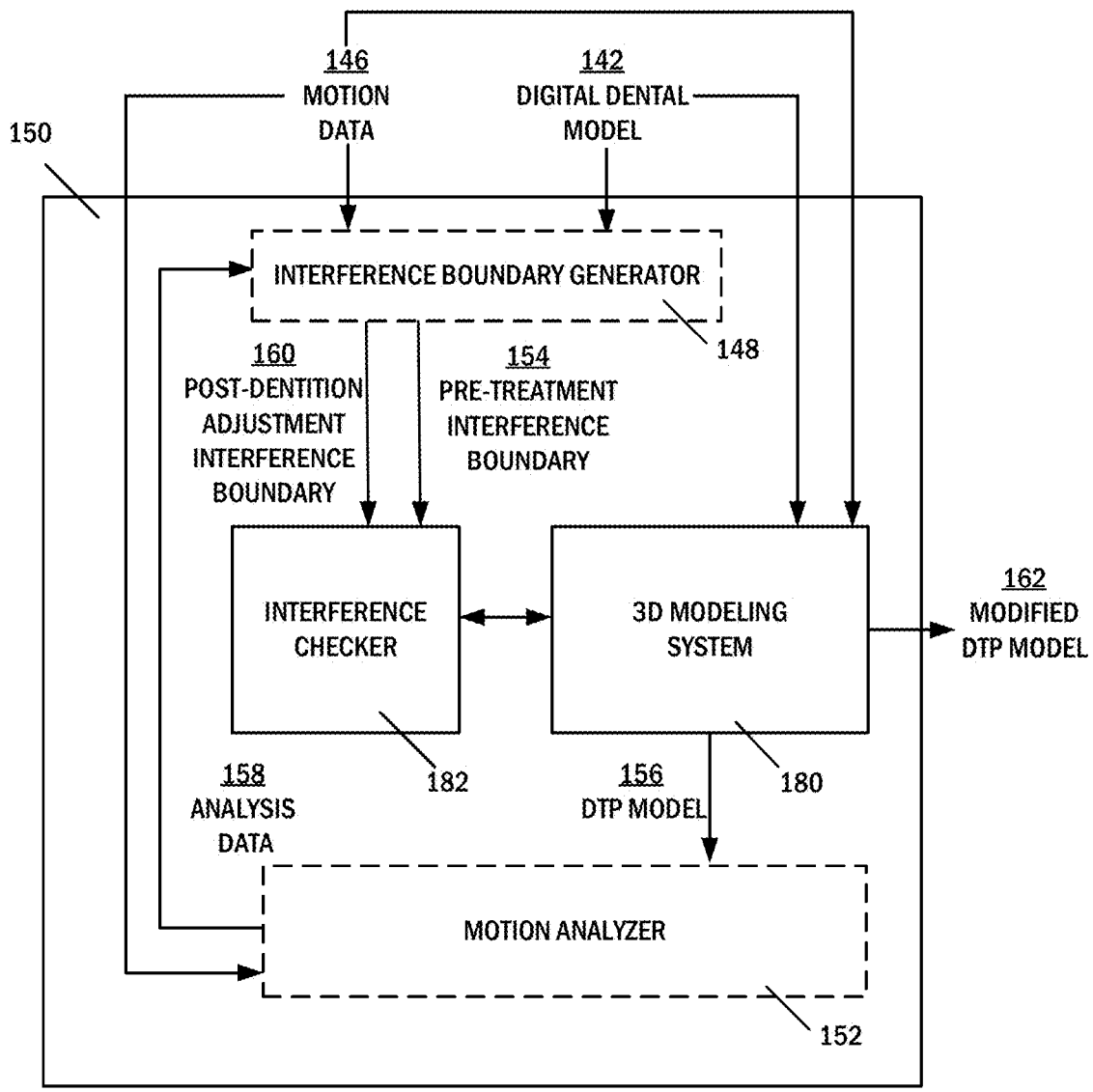
FIG. 4 is a block diagram illustrating an example treatment plan generator of a treatment plan generation system.

FIG. 4 is a block diagram illustrating an example of the treatment plan generator 150 of the treatment plan generation system 130 described in FIG. 3. The treatment plan generator 150 includes one or more components, including at least a three-dimensional (3D) modeling system 180 and an interference checker 182. In some embodiments, treatment plan generator 150 may also include the interference boundary generator 148 and the motion analyzer 152. In other embodiments, the interference boundary generator 148 and the motion analyzer 152 are separate components or sub-systems of the treatment plan generation system 130.

The treatment plan generator 150 determines the dental treatment plan 132. The dental treatment plan 132 includes at least one dentition adjustment 134 for the patient P. Typically, the treatment plan generator 150 operates in cooperation with an operator user, such as the dentist D, to generate the dental treatment plan 132. In some examples, the dental treatment plan 132 is three-dimensional digital data that represents a dental treatment plan (DTP) model 156.

In some embodiments, the 3D modeling system 180 of the treatment plan generator 150 includes computer-aided-design (CAD) software that generates a graphical display of a digital dental model 142 representing dentition of the patient P before the treatment and, either automatically or in cooperation with an operator user, such as the dentist D, generates the DTP model 156 that identifies at least one dentition adjustment 134 to be made from the original digital dental model 142. Example software that can be implemented by the 3D modeling system 180 include 3 Shape CAD/CAM software, Align technology iTero software, Orchestrate Orthodontic Technologies Orchestrate 3D Treatment Planning software, Forestadent Onyx software, and D4D Technologies E4D Dental System, uLab Systems dental aligner planning software, among other similar software. In some embodiments the operator interacts with and manipulates the DTP model 156 to define the dentition adjustment 134 to be made. Additionally, in other embodiments, the 3D modeling system 180 partially or fully automates the generation of the DTP model 156.

In further embodiments, the 3D modeling system 180 can include surgical software that is able to determine a new interference boundary (e.g., the post dentition adjustment interference boundary 160) based on changes to a horizontal and/or vertical position of one or both jaws (e.g., a realignment of the jaws) as a result of various types of surgeries. As one example, when performing a surgery for implant-supported dentures, a portion of the bone is removed from each jaw (e.g., about 0.5 cm from each jaw), which could change the vertical dimension of the jaw. Therefore, a new interference boundary based on the change in vertical dimension can be determined by the software and used to create provisional and/or permanent restorations to be attached to the surgical implant. As another example, when an orthognathic surgery (e.g., corrective jaw surgery) is performed in conjunction with preceding and subsequent dental alignments (e.g., braces), the interference boundary can change as the dimensions of the jaw change. Therefore, multiple new interferences boundaries based on the various stages of change in dimension can be determined by the software (e.g., a boundary post-dental alignment and pre-surgery, a boundary post-surgery, and a boundary post-dental alignment).

In further embodiments, the 3D modeling system 180 comprises digital tools that mimic the tools used by laboratory technicians. Example tools include definition tools, movement tools, alignment tools, segmentation tools, measurement tools, and preparation tools, among other similar tools. In some embodiments, these tools enable a user, such as the dentist D, to interact with and manipulate the digital dental model 142 in accordance with the motion data 146 to develop the dental treatment plan 132 and define the dentition adjustment 134 within the DTP model 156. In other embodiments, the tools may be automated (e.g., do not require user interaction/manipulation).

Definition tools can define the dentition adjustment 134 associated with the dental treatment plan 132. Movement tools can move the patient's dentition according to the motion data 146 (which may be similar to a physical articulator, for example). Alignment tools can be used to simulate an alignment of a tooth or teeth with adjacent and/or opposing teeth based on digital dental model 142. Segmentation tools segment the digital dental model 142 to separate each tooth from adjacent teeth, which is useful, for example, to allow individual teeth (or groups of teeth) within the digital dental model 142 to be moved relative to the other teeth. Measurement tools allow a user, such as dentist D, to perform measurements that may be needed to determine a shape, size, or type of materials that will be needed for a restoration and/or for determining the parameters for the restoration preparation (e.g., how much of and which portion of a tooth to grind, as well as how to shape). Preparation tools enable simulation of at least part of the dental procedure (e.g., a preparation for a restoration) on a tooth or teeth. For example, if the dental procedure is a crown restoration, a tooth may be cut down and shaped within the digital dental model 142 to simulate the crown preparation to be performed.

The interference checker 182 is used by the 3D modeling system 180 to aid in the definition of the dentition adjustment 134 within the DTP model 156 to avoid an adjustment that will cause interference with teeth of the opposing dentition due to a tooth that projects past a pre-treatment interference boundary 154, for example. The pre-treatment interference boundary 154 is a boundary of function between teeth of the dental arch on the upper jaw and teeth of the opposing dental arch on the lower jaw, and is defined by the interface or interaction between the teeth on the opposing dental arches before a treatment plan is implemented. In some embodiments, the interference boundary generator 148 uses the digital dental model 142 and the motion data 146 to determine and provide the pre-treatment interference boundary 154 to the interference checker 182. The interference checker 182 is then used in conjunction with the 3D modeling system 180 to ensure that the dentition adjustment 134 does not move or adjust the tooth or teeth beyond the confines of the pre-treatment interference boundary 154 (e.g., does not violate the pre-treatment interference boundary 154).

If the interference checker 182 identifies a violation of the pre-treatment interference boundary 154 as the 3D modeling system 180 and/or operator user are defining or manipulating the dentition adjustment 134 to generate the DTP model 156 from the original digital dental model 142, an alert may be provided within the graphical display of the digital dental model 142. In some embodiments, the interference checker 182 is also configured to provide color coded indications of violations directly on the graphical display of the digital dental model 142 itself to visually show the operator user where the violations are occurring to help inform the operator how to further modify or manipulate the dentition adjustment 134 to avoid the interference.

However, even with efforts to avoid introducing interference by accounting for interferences caused by the dentition adjustment 134, changes can occur in the patient's jaw motion as a result of the dentition adjustment 134. Such changes in jaw motion can also result in undesirable interference. Therefore, to further bolster efforts to avoid introducing interference, the changes occurring to the patient's jaw motion as a result of the dentition adjustment 134 can also be accounted for by predicting, by the motion analyzer 152, a motion adjustment based on the dentition adjustment 134. In some embodiments, the motion analyzer 152 analyzes the DTP model 156, along with the motion data 146, to predict what changes will occur in the patient's jaw motion as a result of the dentition adjustment 134, and then analyzes the DTP model 156 based on the predicted changes in the patient's jaw motion to generate analysis data 158.

Various embodiments can be implemented by the motion analyzer 152 to predict the motion adjustment. In one or more of the embodiments, a location of a screw axis of the patient's jaw is determined. The screw axis corresponds to the condyloid process of the temporomandibular joint of the patient, and is an axis about which the lower jaw rotates and translates along. Accordingly, the location of the screw axis imposes limitations on a range of motion of the jaw. Mathematical coordinates of the range of motion relative to the patient's dentition can be determined and used as parameters for simulating the motion of the jaw after the dentition adjustment 134 is made. Other jaw-related characteristics or parameters, such as a flexibility or "sponginess" of the temporomandibular joint, can be determined and used as data input for simulating the motion of the jaw. For example, the DTP model 156 that includes the dentition adjustment 134 can be used in conjunction with the screw axis location and other jaw-related parameters to simulate the motion of the jaw after the dentition adjustment 134.

In one embodiment, the motion adjustment prediction is determined via a simulation guided by manual inputs and manipulations of a user, such as the dentist D, to a digital articulator. For example, the digital articulator can be displayed through a user interface of a computing device and the dentist D can interact with the digital articular using input devices of the computing device, such as a touch input device, a mouse, a keyboard, or a joystick, among other input devices. In some embodiments, the digital articulator includes the DTP model 156 defining the dentition adjustment 134, and the user can use the input devices to manually shift the lower jaw of the DTP model 156 within the simulation. The lower jaw is manually shifted up and down, forward and back, and side to side to collect analysis data 158 within the range of motion permitted by the screw axis location and other jaw-related characteristics or parameters for determining whether an interference present in the pre-treatment dentition that restricted the motion of the jaw has been removed as a result of the dentition adjustment 134 defined in the DTP model 156. For example, a post-dentition adjustment interference boundary 160 is determined by the interference boundary generator 148 based on analysis data 158 collected during the manual shifting, and can be compared to the pre-treatment interference boundary 154 to determine whether an interference has been removed.

In another embodiment, the motion adjustment prediction is determined via a simulation employing artificial intelligence to perform automated shifting of the lower jaw of the DTP model 156 within the digital articulator. For example, the lower jaw within the above-described simulation is automatically shifted up and down, forward and back, and side to side within the range of motion permitted by the screw axis location and other jaw-related characteristics or parameters to collect analysis data 158 for determining whether an interference present in the pre-treatment dentition that restricted the motion of the jaw has been removed as a result of the dentition adjustment 134 defined in the DTP model 156. Similarly, the post-dentition adjustment interference boundary 160 is determined by the interference boundary generator 148 based on analysis data 158 collected during the automatic shifting, and can be compared to the pre-treatment interference boundary 154 to determine whether an interference has been removed.

In further embodiments, utilizing the DTP model 156 that includes the dentition adjustment 134 as well as the range of motion limitations designated by the determined screw axis location and other jaw-related characteristics or parameters, data points are recorded at a plurality of different three dimensional points within an xyz space to determine one or more directions and a magnitude thereof that each tooth of the dentition moves as the lower jaw of the DTP model 156 is moved within the xyz space to predict the post-dentition adjustment interference boundary 160. For example, a reference point may be selected within the jaw. From the reference point, a direction and magnitude in which each tooth is able to move is measured as the jaw is moved (e.g., up and down, side to side, and front to back) every n millimeters, for example. In some embodiments, the measurements are relative to a pitch, a yaw, and a roll of the jaw. The analysis data 158 comprises the recorded data points, which are utilized by the interference boundary generator 148 to determine the post-dentition adjustment interference boundary 160, which can be compared to the pre-treatment interference boundary 154 to determine whether an interference has been removed.

The 3D modeling system 180 can then modify the dental treatment plan 132 as needed to accommodate for the predicted motion adjustment (e.g., to ensure that the dentition adjustment 134 made does not go beyond the confines of or violate the predicted post-dentition adjustment interference boundary 160). The 3D modeling system 180 can correspondingly adjust the DTP model 156 to generate a modified DTP model 162. The modified DTP model 162 is then provided as output of the treatment plan generator 150.

Figure 5:
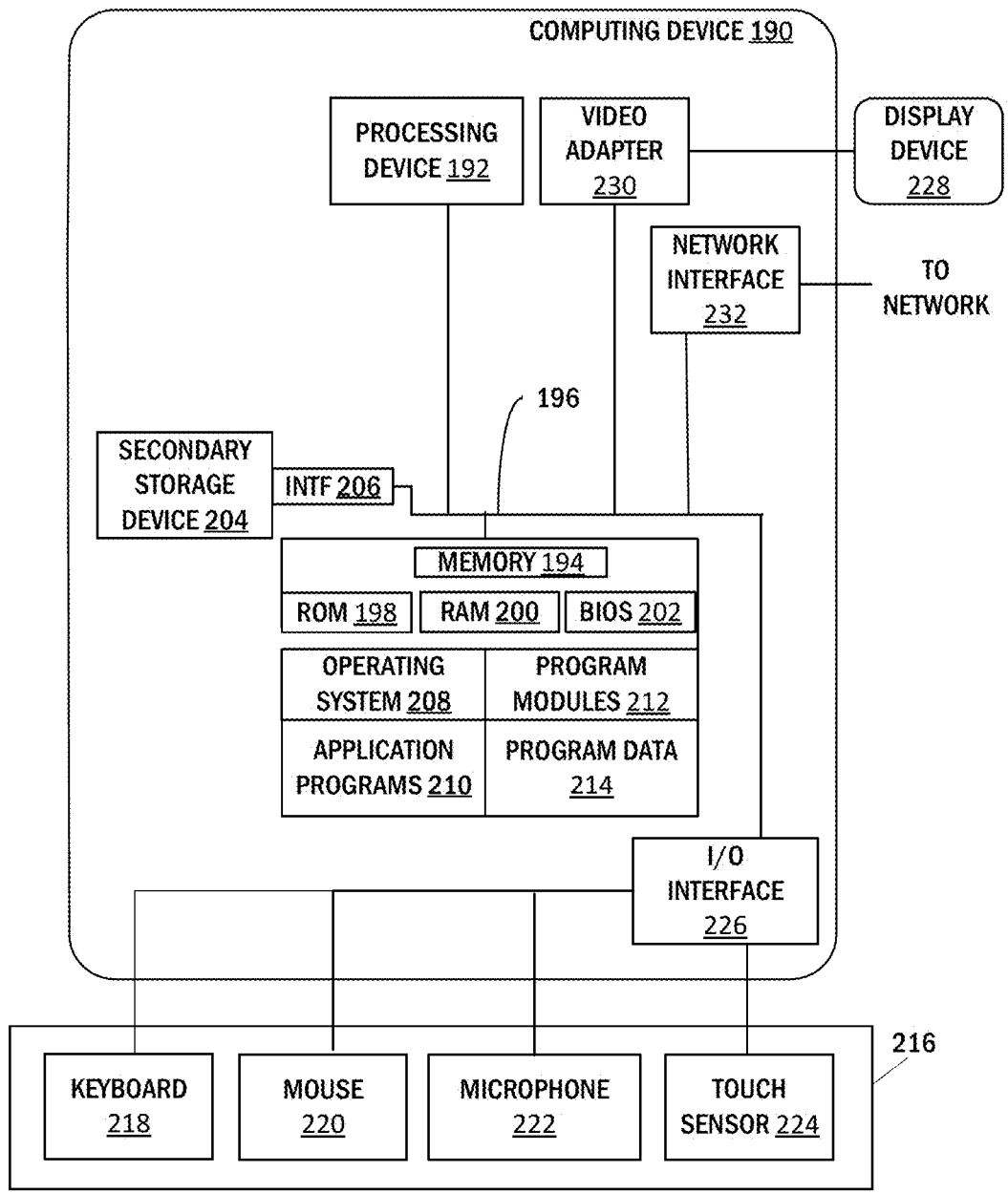
FIG. 5 illustrates an example architecture of a computing device, which can be used to implement aspects according to the present disclosure.

FIG. 5 illustrates an exemplary architecture of a computing device 190 that can be used to implement aspects of the present disclosure, including any of the plurality of computing devices described herein, such as a computing device of the patient evaluation system 120, the scanner 122, the motion capture station 126, the treatment plan generation system 130, the interference boundary generator 148, the treatment plan generator 150, the 3D modeling system 180, the interference checker 182, the motion analyzer 152, the rapid fabrication machine 164, the restoration fabrication station 168, or any other computing devices that may be utilized in the various possible embodiments.

The computing device illustrated in FIG. 5 can be used to execute the operating system, application programs, and software modules (including the software engines) described herein.

The computing device 190 includes, in some embodiments, at least one processing device 192, such as a central processing unit (CPU). A variety of processing devices are available from a variety of manufacturers, for example, Intel or Advanced Micro Devices. In this example, the computing device 190 also includes a system memory 194, and a system bus 196 that couples various system components including the system memory 194 to the processing device 192. The system bus 196 is one of any number of types of bus structures including a memory bus, or memory controller; a peripheral bus; and a local bus using any of a variety of bus architectures.

Examples of computing devices suitable for the computing device 190 include a desktop computer, a laptop computer, a tablet computer, a mobile computing device (such as a smart phone, an iPod® or iPad® mobile digital device, or other mobile devices), or other devices configured to process digital instructions.

The system memory 194 includes read only memory 198 and random access memory 200. A basic input/output system 202 containing the basic routines that act to transfer information within computing device 190, such as during start up, is typically stored in the read only memory 198.

The computing device 190 also includes a secondary storage device 204 in some embodiments, such as a hard disk drive, for storing digital data. The secondary storage device 204 is connected to the system bus 196 by a secondary storage interface 206. The secondary storage device 204 and their associated computer readable media provide non-volatile storage of computer readable instructions (including application programs and program modules), data structures, and other data for the computing device 190.

Although the exemplary environment described herein employs a hard disk drive as a secondary storage device, other types of computer readable storage media are used in other embodiments. Examples of these other types of computer readable storage media include flash memory cards, digital video disks, compact disc read only memories, digital versatile disk read only memories, random access memories, or read only memories. Some embodiments include non-transitory media. Additionally, such computer readable storage media can include local storage or cloud-based storage.

A number of program modules can be stored in secondary storage device 204 or system memory 194, including an operating system 208, one or more application programs 210, other program modules 212 (such as the software engines described herein), and program data 214. The computing device 190 can utilize any suitable operating system, such as Microsoft Windows™, Google Chrome™ OS, Apple OS, Unix, or Linux and variants and any other operating system suitable for a computing device. Other examples can include Microsoft, Google, or Apple operating systems, or any other suitable operating system used in tablet computing devices.

In some embodiments, a user provides inputs to the computing device 190 through one or more input devices 216. Examples of input devices 216 include a keyboard 218, mouse 220, microphone 222, and touch sensor 224 (such as a touchpad or touch sensitive display). Other embodiments include other input devices 216. The input devices are often connected to the processing device 192 through an input/output interface 226 that is coupled to the system bus 196. These input devices 216 can be connected by any number of input/output interfaces, such as a parallel port, serial port, game port, or a universal serial bus. Wireless communication between input devices and the input/output interface 226 is possible as well, and includes infrared, BLUETOOTH® wireless technology, IEEE 802.11a/b/g/n, cellular, ultra-wideband (UWB), ZigBee, LoRa, or other radio frequency communication systems in some possible embodiments.

In this example embodiment, a display device 228, such as a monitor, liquid crystal display device, projector, or touch sensitive display device, is also connected to the system bus 196 via an interface, such as a video adapter 230. In addition to the display device 228, the computing device 190 can include various other peripheral devices (not shown), such as speakers or a printer.

When used in a local area networking environment or a wide area networking environment (such as the Internet), the computing device 190 is typically connected to the network through a network interface 232, such as an Ethernet interface. Other possible embodiments use other communication devices. For example, some embodiments of the computing device 190 include a modem for communicating across the network.

The computing device 190 typically includes at least some form of computer readable media. Computer readable media includes any available media that can be accessed by the computing device 190. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 190.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 5 is also an example of programmable electronics, which may include one or more such computing devices, and when multiple computing devices are included, such computing devices can be coupled together with a suitable data communication network so as to collectively perform the various functions, methods, or operations disclosed herein.

Figure 6:
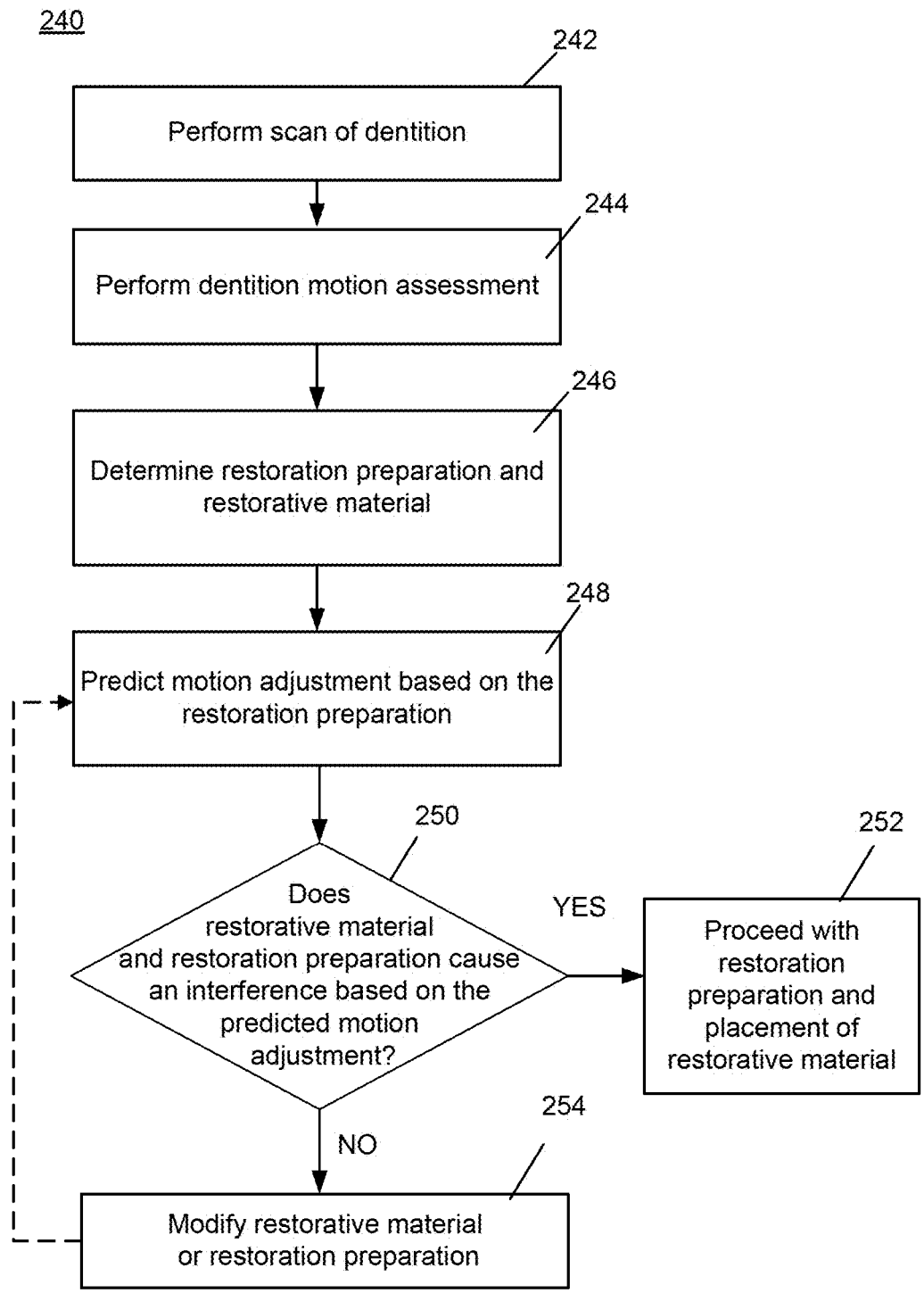
FIG. 6 is a flow chart illustrating an example method of predicting a motion adjustment responsive to a restoration preparation.

FIG. 6 is a flow chart illustrating an example method 240 of predicting a motion adjustment responsive to a restoration preparation. In this example, the method 240 includes operations 242, 244, 246, 248, 250, 252, and 254. Example dental procedures involving dentition adjustments may include dental restorations and dental alignment. The first example is illustrated and described in more detail with reference to FIG. 6, and the second example is illustrated and described in more detail with reference to FIG. 7.

Often, dental restorations involve two steps: preparation of the tooth or teeth for placement of restorative materials (i.e., a restoration preparation) and the placement of the restorative materials. Example dental restorations include dental implants, bridges, and/or crowns, among other similar dental procedures. The example method 240 can be implemented by various components of the patient evaluation system 120 described above with reference to FIGS. 2 through 4.

At operation 242, a scan 124 of dentition is performed prior to the preparation and/or placement of the restorative materials. Based on the scan 124, a position and orientation of each tooth in the upper and lower dental arches of the dentition is determined with respect to each other tooth. At operation 244, a dentition motion assessment 128 is performed. The dentition motion assessment 128 captures a representation of the movement of the dental arches relative to each other. For example, the dentition motion assessment 128 captures how each tooth in the upper and lower dental arches move with respect to one another.

An interference boundary prior to the restoration preparation (e.g., a pre-treatment interference boundary 154) can be determined from the scan 124 and the dentition motion assessment 128. The pre-treatment interference boundary 154 is a boundary of function between teeth of the dental arch on the upper jaw and teeth of the opposing dental arch on the lower jaw, and is defined by the interface or interaction between teeth on opposing dental arches. For example, the pre-treatment interference boundary 154 indicates how far each particular tooth can vertically, anteroposteriorly, and transversely. If a tooth extends or crosses over the pre-treatment interference boundary in one or more planes, an interference with teeth of the opposing dental arch of the dentition is created.

At operation 246, a restorative material and a restoration preparation are determined. The restoration preparation can involve a removal and/or shaping of one or more portions of a tooth or teeth. In one example, the restoration preparation is a crown preparation that involves grinding off a top part of the tooth to replace with a crown. In another example, the restoration preparation is a bridge preparation that involves grinding off a top part of multiple teeth to replace with a bridge. In a further example, the restoration preparation is a dental implant preparation that involves removal of the entire tooth to be replaced with an implant.

In some examples, the restoration preparation is determined using the scan 124, data from the dentition motion assessment 128, and the determined pre-treatment interference boundary 154. For example, a position and orientation of a tooth associated with the restoration is visualized using the scan 124 and motion data 146 to determine how the tooth associated with the restoration preparation can move vertically, anteroposteriorly, and transversely ensure that the how the tooth is prepared (e.g., what portions of the tooth are being removed or how the tooth is shaped) does not move or adjust the tooth beyond the confines of or violate the pre-treatment interference boundary 154 to avoid introducing an interference.

The determination of the restorative material includes determining a type of material to use to replace or cover the one or more portions of the tooth or teeth removed and/or shaped in the restoration preparation. Based on a type of the restoration preparation, certain types of restorative material can be more advantageous to use due to the properties of the materials, such as a durability of the material or a malleability of the material. A size of the material, including a thickness of material, can also be determined.

At operation 248, a motion adjustment based on the restoration preparation is predicted. As one example, if the restoration preparation determined at operation 246 is a crown preparation that will require the cutting or grinding down of a tooth or set of teeth, the additional space provided by the crown preparation may actually modify the patient's bite and jaw motion by removing an interference that had been previously restricting the motion of the jaw. This modification to the bite and jaw motion may result in the need to further modify the restoration preparation and/or restorative materials determined at operation 246 to avoid interferences resulting from the modifications. For example, the jaw can now move more freely in one or more directions causing the teeth to move relative to one another in different ways (e.g., a particular tooth can now move further vertically, anteroposteriorly, or transversely). Accordingly, the motion adjustment can affect the pre-treatment interference boundary 154.

Therefore, to predict the motion adjustment, a determination is made as to whether an interference will be removed after the restoration preparation, and if so, associated effects of the removal by predicting a post-preparation interference boundary. The post-preparation interference boundary is defined by the interface or interaction between the teeth on the opposing dental arches after the restoration preparation is performed. In some examples, the post-preparation interference boundary can be compared to the pre-treatment interference boundary 154 to measure a change that has occurred, where the change (e.g., a net reduction) between the two interference boundaries can be used to determine whether the dentition has been sufficiently prepared for the placement of the restorative material. Continuing the above example of a crown preparation, a particular amount of reduction (e.g., cutting or grinding down of the tooth) is required so that a restorative material of a sufficient thickness (e.g., for stability) can be placed over the prepared tooth without causing interference. In other words, the particular amount of reduction during preparation with placement of the sufficiently thick restorative material thereon meets a required clearance to avoid interference.

At decision 250, a determination is made as to whether the restorative material and the restoration preparation cause an interference based on the predicted motion adjustment. The determination can be made based on the measured change between the pre-treatment interference boundary 154 and the post-preparation interference boundary predicted discussed above in conjunction with operation 248. As previously discussed, dental restoration involves two steps: preparation of the tooth for placement of restorative materials (i.e., restoration preparation) and the placement of the restorative materials. Restoration preparation includes a change to a structure or shape of a tooth or teeth. For example, grinding down a tooth to a certain size and shape, so that it may be covered with restorative material (e.g. a crown) or extracting one or more teeth for installation of a dental implant or a bridge. As described above with respect to operation 246, the restoration preparation and restorative materials are determined based on the pre-treatment interference boundary 154 to avoid introducing interference. For example, the restoration preparation and restorative materials are initially determined to meet a required clearance, which ensures a proper fit enabling the patient P to maintain a same or similar bite pre-treatment and post-dentition adjustment (e.g., a tooth and restorative material when placed over the tooth does not extend or cross over the pre-treatment interference boundary 154 in one or more planes to avoid introducing interference). However, any adjustments to the motion of the jaw resulting from the restoration preparation of the tooth (e.g., due to a removal of an interference) can correspondingly impact how the tooth should be prepared and/or how the restorative materials should be placed. For example, if an interference is removed by the restoration preparation and the motion of the jaw changes, the required clearance could either increase or decrease in size due to a change in the pre-treatment interference boundary 154, and the restoration preparation and restorative materials may no longer avoid interference. As one example, when the changes in jaw motion cause the required clearance to decrease in size (e.g., when a space in which the restorative material placed over the prepared tooth is designed to fit has decreased), a vertical height of the restorative material, such as a crown, may now be too tall for the space causing a new interference with opposing teeth.

If the restorative material and the restoration preparation do not cause an interference based on the predicted motion adjustment (e.g., based on the measured change between the pre-treatment interference boundary 154 and the post-preparation interference boundary), the restoration preparation is performed and the restorative material is placed at operation 252. For example, the portions of the tooth are removed and/or shaped according to the initial restoration preparation determined, and the portions removed can be replaced with the initial restorative materials determined.

If the restorative material and the restoration preparation cause an interference based on the predicted motion adjustment (e.g., based on the measured change between the pre-treatment interference boundary 154 and the post-preparation interference boundary), one or more of the restorative material and the restoration preparation are modified at operation 254. For example, the restoration preparation and/or restorative material are modified to correspond to the predicted post-preparation interference boundary. In one embodiment, a size or a thickness of the restorative material can be modified or a different type of restorative material can be used. For example, if it is predicted that the restoration preparation will remove an interference and cause a motion adjustment of the jaw that lowers a height of clearance for the restorative materials being placed (e.g., the motion adjustment brings upper and lower dentition closer together leaving less space for the restorative material), a size or thickness of the restorative material is reduced. However, in some cases, properties of the restorative material cannot be reduced below a certain size or thickness and thus a new restorative material will be selected. In another embodiment, the restoration preparation itself is adjusted. For example, a tooth being prepared can be ground or cut down to a different height or shape that will enable the restorative material to be placed. In a further embodiment, both the restorative material and the restoration preparation are modified.

In additional embodiments, when the restoration preparation includes a crown preparation and the restorative material is a crown, the crown can be automatically generated to account for the motion adjustment. For example, an occlusal surface of the crown may be generated digitally to correspond with the predicted post-preparation interference boundary. In some embodiments, a default crown structure is used as a starting template that is then adjusted and contoured based on the predicted post-preparation interference boundary. Specifically, the predicted post-preparation interference boundary is used to define contoured portions of the crown surface that interface with opposing and adjacent teeth to prevent introducing interference. For example, based on the predicted post-preparation interference boundary, one or more rules or parameters are generated to ensure that the boundary is not violated in any plane by the crown as it is being digitally generated. In some examples, the rules or parameters may be associated with a slope of the sidewalls of the crown, in addition to a height and shape of the crown.

In some embodiments, the operations 248, 250, and 254 can be repeated one or more times until the restorative material and the restoration preparation do not cause an interference. The process can be iteratively repeated to modify the restorative material or restoration preparation, predict motion based on the modified restoration preparation, and further modify the restorative material or restoration reparation based on whether the restorative material and restoration preparation cause an interference based on the predicted motion.

Figure 7:
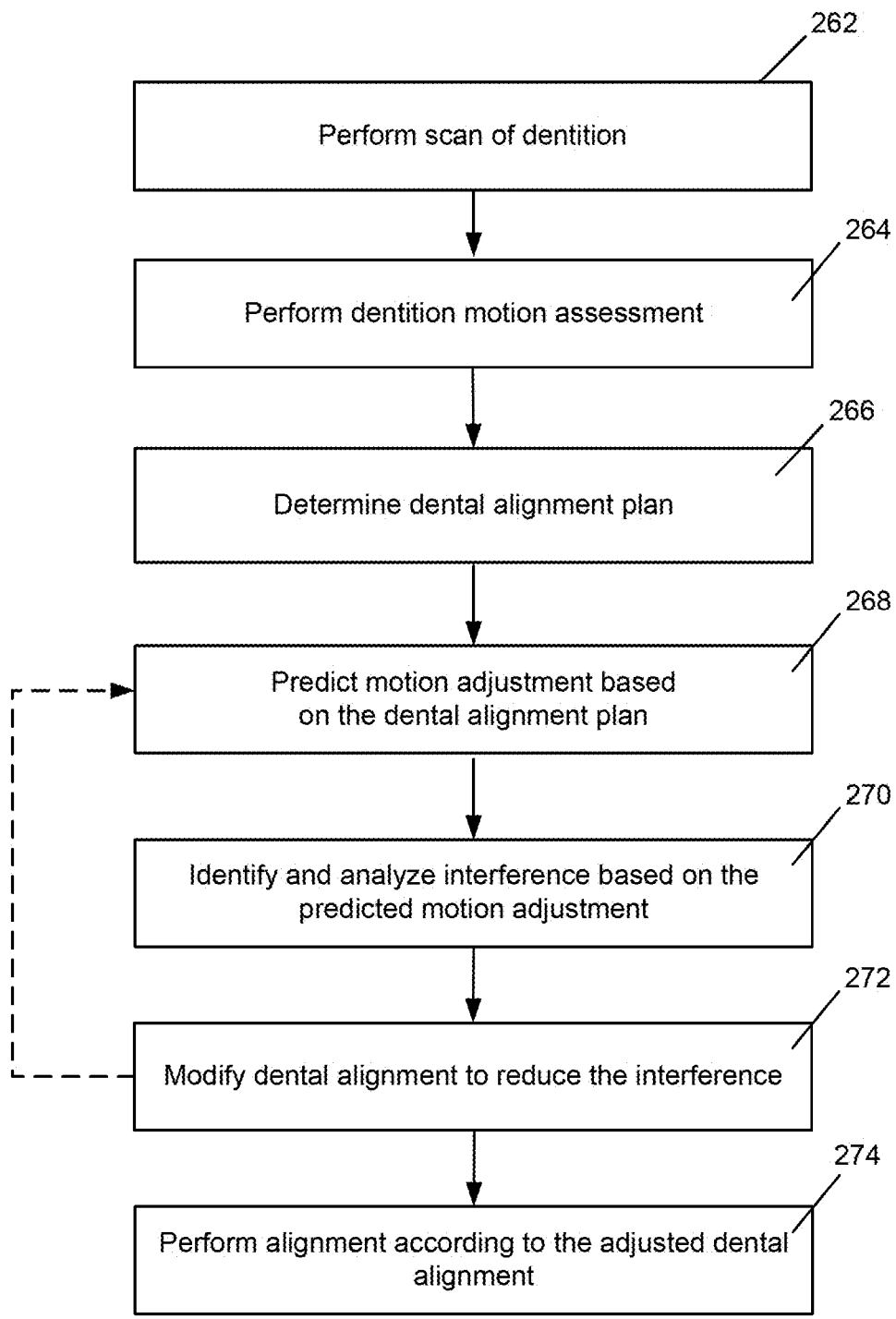
FIG. 7 is a flow chart illustrating an example method of predicting a motion adjustment responsive to a dental alignment plan.

FIG. 7 is a flow chart illustrating an example method 260 of predicting a motion adjustment responsive to a dental alignment plan. The dental alignment plan involves adjustment of position and/or alignment of the teeth in three planes of space, which can be accomplished using braces, retainers, or other dental alignment tools. The example method 260 can be implemented by various components of the patient evaluation system 120 described above in FIGS. 2 through 4. In this example, the method 260 includes operations 262, 264, 266, 268, 270, 272, and 274.

At operation 262, a scan 124 of dentition is performed. Based on the scan 124, a position and orientation of each tooth in the upper and lower dental arches is determined with respect to each other tooth. At operation 264, a dentition motion assessment 128 is performed. The dentition motion assessment 128 captures a representation of the movement of the dental arches relative to each other. For example, the dentition motion assessment 128 captures how each tooth in the upper and lower dental arches move with respect to one another. The movement is captured as motion data 146.

Using the scan 124 and motion data 146, an interference boundary prior to the dental alignment (e.g., a pre-treatment interference boundary 154) can be determined. The pre-treatment interference boundary 154 is a boundary of function between teeth of the dental arch on the upper jaw and teeth of the opposing dental arch on the lower jaw, and is defined by the interface or interaction between teeth on opposing dental arches. For example, the pre-treatment interference boundary 154 indicates how far a particular tooth can move vertically, anteroposteriorly, and transversely. If a tooth extends or crosses over the pre-treatment interference boundary 154 in one or more planes, an interference with teeth of the opposing dental arch of the dentition is created.

At operation 266, a dental alignment plan is determined using the scan 124 of the dentition, motion data 146 from the dentition motion assessment 128, and the pre-treatment interference boundary 154. For example, utilizing the scan 124 and motion data 146, a position and orientation of a tooth associated with the alignment and how the tooth can move vertically, anteroposteriorly, and transversely can be visualized to ensure that how the tooth is aligned (e.g., a direction or orientation of the alignment) does not move or adjust the tooth beyond the confines of the pre-treatment interference boundary 154 to avoid introducing an interference.

At operation 268, a motion adjustment based on the dental alignment plan is predicted. As one example, if the dental alignment plan determined at operation 266 involves straightening a crooked tooth, the new position and orientation of the straight tooth can cause the patient's bite and jaw motion to change. This change to the bite and jaw motion may result in the need to further modify the dental alignment plan determined at operation 246 to avoid interferences resulting from the changes. For example, the motion of the jaw may be more restricted in one or more directions causing the teeth to move relative to one another in different ways. For example, the tooth once straightened can no longer move as far vertically, anteroposteriorly, or transversely before interfacing with opposing teeth. Accordingly, the motion adjustment can affect the pre-treatment interference boundary 154.

Therefore, to predict the motion adjustment, a determination is made as to whether an interference will be removed or created following the dental alignment and if so, associated effects of the removal by predicting a post-alignment interference boundary (e.g., the interference boundary after the dental alignment). The post-alignment interference boundary is defined by the interface or interaction between the teeth on the opposing dental arches after the dental alignment.

At operation 270, an interference is identified and analyzed based on the predicted motion adjustment. For example, in some embodiments, the interference is identified and analyzed by comparing the pre-treatment interference boundary 154 to the post-alignment interference boundary.

At operation 272, the dental alignment is modified to reduce the interference. For example, the dental alignment plan is modified and the modified dental alignment can be further analyzed to see if the interference has been removed. If not, the plan can be iteratively modified until the interference has been eliminated or is less than a predetermined threshold amount. For example, the operations 268, 270, and 272 can be repeated one or more times to adjust the dental alignment, predict motion based on the adjusted dental alignment, identify and analyze interference based on the predicted motion, and further adjust the dental alignment based on identified interference until interference is eliminated, or until the interference is less than a predetermined amount. Once the interference is eliminated, or the interference is less than the predetermined amount, the dental alignment can be performed according to the adjusted dental alignment at operation 274.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A method of analyzing a dental treatment plan, the method comprising:
   performing a scan of a dentition;
   performing a dentition motion assessment, wherein the motion assessment includes capturing motion data representing movement of a patient's opposing dental arches relative to each other;
   determining a pre-treatment interference boundary based on the scan and the dentition motion assessment, wherein the pre-treatment interference boundary comprises a boundary of function between teeth of the opposing dental arches before implementing the dental treatment plan;
   determining the dental treatment plan with a dentition adjustment based on the scan, the dentition motion assessment, and the pre-treatment interference boundary,
   wherein the dental treatment plan is designed to not violate the pre-treatment interference boundary;
   predicting a motion adjustment based on the dentition adjustment; and
   modifying the dental treatment plan based on the predicted motion adjustment.

2. The method of claim 1, wherein the pre-treatment interference boundary is further defined by an interface or interaction between the opposing teeth.

3. The method of claim 2, further comprising:
determining the dental treatment plan with the dentition adjustment based on the pre-treatment interference boundary to avoid introducing interferences between the opposing teeth.

4. The method of claim 1, wherein predicting the motion adjustment based on the dentition adjustment comprises:
predicting a post-dentition adjustment interference boundary, wherein the post-dentition adjustment interference boundary is a boundary of function between opposing teeth of upper and lower dental arches after the dentition adjustment has been performed, and is defined by an interface or interaction between the opposing teeth.

5. The method of claim 1, wherein modifying the dental treatment plan based on the predicted motion adjustment comprises:
in response to determining that the dentition adjustment of the dental treatment plan causes the motion adjustment, modifying the dental treatment plan to accommodate the predicted motion adjustment.

6. A patient evaluation system for analyzing a dental treatment plan, the system comprising:
a scanner configured to perform a scan of a dentition;
a motion capture station configured to perform a dentition motion assessment; and a treatment plan generation system configured to:
determine a pre-treatment interference boundary based on the scan and the dentition motion assessment, wherein the pre-treatment interference boundary comprises a boundary of function between teeth of a patient's opposing dental arches before implementing the dental treatment plan;
determine the dental treatment plan with a dentition adjustment based on the scan, the dentition motion assessment, and the pre-treatment interference boundary,
wherein the dental treatment plan is designed to not violate the pre-treatment interference boundary; and
predict a motion adjustment based on the dentition adjustment; and modify the dental treatment plan based on the predicted motion adjustment.

7. The system of claim 6, wherein the treatment plan generation system comprises an interference boundary generator configured to:
determine the pre-treatment interference boundary based on a digital dental model generated from the scan and motion data captured from the dentition motion assessment, the digital dental model representing a position and an orientation of each tooth in upper and lower dental arches of the dentition with respect to each other tooth, and the motion data representing a movement of the upper and lower dental arches of the dentition relative to each other; and
predict a post-dentition adjustment interference boundary based on the predicted motion adjustment.

8. The system of claim 7, wherein the treatment plan generation system comprises a treatment plan generator configured to:
determine the dental treatment plan with the dentition adjustment based on the pre-treatment interference boundary; and
modify the dental treatment plan based on the predicted post-dentition adjustment interference boundary.

9. The system of claim 6, wherein the treatment plan generation system comprises a motion analyzer configured to:
predict the motion adjustment by:
determining a location of a screw axis about which a lower jaw rotates and translates along;
determining one or more other jaw-related parameters; and simulating a range of motion of a jaw in a digital dental model that
includes the dentition adjustment, the range of motion based on the location of the screw axis and the one or more other jaw-related parameters.

10. The system of claim 9, wherein the motion analyzer comprises a digital articulator displayed through a user interface of a computing device, the digital articulator including the digital dental model that includes the dentition adjustment, wherein one or more of:
a user interacts with the digital articulator using input devices of the computing device to manually shift the lower jaw within the digital dental model to predict the motion adjustment; and
artificial intelligence is implemented to perform automated shifting of the lower jaw within the digital dental model to predict the motion adjustment.

11. The system of claim 9, wherein the motion analyzer records data points at a plurality of three dimensional points within an xyz space to determine one or more directions and a magnitude thereof that each tooth of the dentition moves as the lower jaw of the digital dental model is moved within the xyz space to predict the motion adjustment.

12. A method of dental alignment, the method comprising:
performing a scan of a dentition;
performing a dentition motion assessment;
determining a pre-treatment interference boundary based on the scan and the dentition motion assessment, wherein the pre-treatment interference boundary comprises a boundary of function between teeth of opposing dental arches before implementing the dental treatment plan;
determining a dental alignment plan based on the scan, the dentition motion assessment, and the pre-treatment interference boundary,
wherein the dental alignment plan is designed to not violate the pre-treatment interference boundary;
predicting a motion adjustment based on the dental alignment plan;
identifying and analyzing interference based on the predicted motion adjustment; and
modifying the dental alignment plan to reduce the interference.

13. The method of claim 12, wherein identifying and analyzing the interference based on the predicted motion adjustment comprises:
comparing the pre-treatment interference boundary determined based on the scan and the dentition motion assessment to a post-alignment interference boundary predicted by analyzing the dental alignment plan and motion data captured by the dentition motion assessment to identify the interference.

* * * * *